(12) United States Patent
Nakamura

(10) Patent No.: US 7,598,424 B2
(45) Date of Patent: Oct. 6, 2009

(54) PROCESS FOR PRODUCTION OF BISPHENOL A

(75) Inventor: Hideaki Nakamura, Takaishi (JP)

(73) Assignee: Mitsui Chemicals, Inc., Tokyo (JP)

( * ) Notice: Subject to any disclaimer, the term of this patent is extended or adjusted under 35 U.S.C. 154(b) by 510 days.

(21) Appl. No.: 10/542,797

(22) PCT Filed: Mar. 25, 2004

(86) PCT No.: PCT/JP2004/004148

§ 371 (c)(1), (2), (4) Date: Jul. 20, 2005

(87) PCT Pub. No.: WO2004/085357

PCT Pub. Date: Oct. 7, 2004

(65) Prior Publication Data

US 2006/0183949 A1   Aug. 17, 2006

(30) Foreign Application Priority Data

Mar. 27, 2003  (JP) ............................. 2003-086872

(51) Int. Cl.
     *C07C 39/16* (2006.01)
(52) U.S. Cl. ................................... 568/728
(58) Field of Classification Search .................. 568/728
     See application file for complete search history.

(56) References Cited

U.S. PATENT DOCUMENTS 5,314,506 A    5/1994  Midler, Jr. et al.
5,545,764 A    8/1996  Berg et al.
6,355,218 B1   3/2002  Zorge et al.

FOREIGN PATENT DOCUMENTS

| EP | 0 671 377 A1 | 9/1995 |
|---|---|---|
| EP | 0 718 268 A2 | 6/1996 |
| JP | 5-117191 A | 5/1993 |
| JP | 07-025798 A | 1/1995 |
| JP | 7-258131 A | 10/1995 |
| JP | 2003-528840 A | 9/2003 |
| WO | WO 01/72677 A1 * | 3/2001 |
| WO | WO-01/72677 A1 | 10/2001 |

* cited by examiner

*Primary Examiner*—Daniel M Sullivan
*Assistant Examiner*—Kellette Gale
(74) *Attorney, Agent, or Firm*—Birch, Stewart, Kolasch & Birch, LLP

(57) ABSTRACT

An object of present invention is to provide a process of producing bisphenol A, and more particularly a process of producing bisphenol A having high purity and an excellent hue.

In the present invention, in a crystallization step to form the slurry containing adduct crystals,
  (a) a fed solution of bisphenol A in phenol is cooled at the temperatures of at least two steps to form a slurry containing adduct crystals,
  (b) at least two crystallization stages having different cooling temperatures are provided, and
  (c) when the solid fraction of the slurry is A [% by weight] in the final crystallization stage prior to transporting the slurry into the solid-liquid separation step and the solid fraction of the slurry is B [% by weight] in the crystallization stage in which crystals are first formed, the value of B/A is kept 0.7 or less.

9 Claims, No Drawings

PROCESS FOR PRODUCTION OF BISPHENOL A

TECHNICAL FIELD

The present invention relates to a process of producing bisphenol A. More particularly, the present invention relates to a process of producing bisphenol A having excellent economical efficiency, high purity and an excellent hue.

BACKGROUND ART

Bisphenol A [2,2'-bis(4-hydroxyphenyl)propane] has been used as a starting material for producing a variety of polymers. In recent years, there has especially been a high demand for aromatic polycarbonates having excellent impact resistance and transparency, and bisphenol A having low coloring has been desired for producing aromatic polycarbonates.

Bisphenol A is usually produced by reacting phenol with acetone in the presence of homogenous acids or solid acid catalysts. The reaction mixture includes unreacted acetone, unreacted phenol, water produced during the reaction, and other side-products in addition to bisphenol A. The main component of the side-products is 2-(2-hydroxyphenyl)-2-(4-hydroxyphenyl)propane (hereinafter, referred to as "o,p'-BPA"), and in addition, the side-products include trisphenol, a polyphenol compound, a chroman compound, colored impurities and the like.

Bisphenol A is obtained by cooling the reaction mixture to form a slurry containing a crystalline adduct of phenol-bisphenol A (hereinafter, referred to as "adduct crystals"), if necessary, after removing unreacted acetone and water produced during the reaction and concentrating bisphenol A [a crystallization step], separating the adduct crystals from the slurry [a solid-liquid separation step], washing the separated adduct crystals with phenol, etc. [a washing step], and then removing phenol by means of distillation or stripping.

As described above, the reaction mixture of bisphenol A contains colored impurities. In the steps of producing bisphenol A, the main step of removing the colored impurities includes the crystallization step, the solid-liquid separation step, and the washing step. The purity and the hue of the adduct crystals produced in the crystallization step give an effect on the purity and the hue of the bisphenol A product. Further, when the adduct crystals produced in the crystallization step are fine crystals, the amount of a mother liquor adhered to the surface of crystals per unit weight of crystals is increased. There is also deterioration in the separation efficiency of colored impurities in the solid-liquid separation step and the washing step subsequent thereto. Accordingly, in order to produce bisphenol A, it is important to produce adduct crystals having high purity and good hue and generating a small amount of fine crystals in a crystallization step.

As a method of producing adduct crystals with high purity and excellent hue, there can be mentioned a method comprising, by using a series of multi-stage crystallization tanks, sequentially cooling to the targeted final temperature, as described in Japanese Unexamined Patent Application Publication No. 5-117191, Japanese Unexamined Patent Application Publication No. 7-258131, and PCT Japanese Translation Patent Publication No. 2003-528840. However, this method does not disclose the ratio (=B/A[–]) of a solid fraction B [% by weight] in the final crystallization stage to a solid fraction A [% by weight] in the first crystallization stage, which is required to obtain adduct crystals having high purity as disclosed in the present invention. Further, this method is insufficient for producing adduct crystals having high purity, good hue, and a small amount of fine crystals.

Japanese Unexamined Patent Application Publication No. 5-117191 discloses a method comprising, by using n-number of crystallization towers having an inner cylinder provided with an inlet port at its upper portion, discharging a part of the slurry of adduct crystals in the crystallization towers, cooling the discharged slurry in a heat exchanger provided at the outside of the crystallization towers, and then recycling the slurry of adduct crystals into the crystallization tower, and at the same time at least a part of the slurry of adduct crystals in the n-th stage is heated to dissolve fine crystals and is then recycled into the crystallization tower. However, since the adduct crystals are easily crushed, the adduct crystals are crushed during circulation of the slurry, which inevitably leads to the formation of fine crystals. In addition, it is necessary to heat the slurry of adduct crystals having been once cooled, thereby causing energy loss.

Japanese Unexamined Patent Application Publication No. 7-258131 discloses a method in which, by using an n-stage cascade of crystallization tanks connected in series with the number of crystallization reactors n (where n>1), the reaction mixture is circulated at a circulation rate of at least 500 m$^3$/h in a state where the residence time in each crystallization device is set to three hours or more. In this method, a plurality of crystallization devices which has a residence time of at least 3 hours is required, thereby increasing the cost for their equipment. Further, since a circulation rate of 500 m$^3$/hr or more is required, a great amount of power is required. Furthermore, in the case where the circulation of the slurry is performed at such a large circulation rate, the amount of fine crystals produced by crushing the adduct crystals becomes large.

PCT Japanese Translation Patent Publication No. 2003-528840 discloses a process of producing adduct crystals using crystallization devices of one to five stages during a residence time of 2 to 12 hours, by using one or more crystallization devices having a crystallization tank, a circulating pump and a cooler. In this method, each crystallization device also needs a circulating pump and the adduct crystals are thus crushed by the circulating pump, thereby forming fine crystals. In addition, the hue of bisphenol A obtained by removing phenol from the adduct crystals becomes insufficient.

As such, in the conventional known method comprising sequentially cooling the reaction mixture to the targeted final crystallization temperature by using a series of multi-stage crystallization tanks, the ratio (B/A) of a solid fraction B in the final crystallization stage to a solid fraction A in the first crystallization stage which is required to obtain adduct crystals having high purity is not disclosed. In addition, from the view point of equipment investment, it is known that the crystallization devices practically having three or less crystallization stages and preferably two crystallization stages are preferable. In such method, there is a problem that it is difficult to precisely control the temperature according to a growth process of crystals, since the temperature of the slurry in one crystallization device is approximately homogenous. Therefore, it is not possible to precisely control the temperature according to a growth process of crystals.

The present invention relates to a process of producing bisphenol A. More particularly, it is an object of the present invention to provide a process of producing bisphenol A having excellent economical efficiency, high purity and an excellent hue.

DISCLOSURE OF THE INVENTION

The present inventors have made extensive and intensive studies for solving the above-mentioned problems. As a result, it has been found that, when a solution of bisphenol A in phenol is cooled at the temperatures of at least two steps to continuously form adduct crystals, the adduct crystals having high purity and a good hue can be obtained by setting a ratio (B/A) of a solid fraction B [% by weight] in the final crystallization stage to a solid fraction A [% by weight] in the first crystallization stage to a specific range. It has also been found that the adduct crystals can be continuously and economically obtained by cooling a solution of bisphenol A in phenol using a multi-chamber type crystallization device having its inside divided into 3 or more compartments by partitions with at least one of the compartments equipped with a cooler. The present invention has thus been completed on the basis of the findings.

That is, the present invention provides a process of producing bisphenol A comprising:

(1) a step of producing a phenolic solution containing bisphenol A by reacting phenol with acetone, (2) a crystallization step of cooling the obtained phenolic solution containing bisphenol A in a crystallization device and continuously forming a slurry containing adduct crystals comprising phenol and bisphenol A, (3) a solid-liquid separation step of separating the adduct crystals from the formed slurry, and (4) a step of producing bisphenol A by removing phenol from the separated adduct crystals, wherein, in the crystallization step, (a) the fed solution of bisphenol A in phenol is cooled at the temperatures of at least two steps to form a slurry containing adduct crystals, (b) at least two crystallization stages having different cooling temperatures are provided, and (c) when the solid fraction of the slurry is A [% by weight] in the final crystallization stage prior to feeding the slurry into said solid-liquid separation step and is B [% by weight] in the crystallization stage in which crystals are first formed, the value of B/A is kept at 0.7 or less.

Furthermore, the present invention provides a process of producing bisphenol A comprising:

(1) a step of producing a phenolic solution containing bisphenol A by reacting phenol with acetone, (2) a crystallization step of cooling the obtained phenolic solution containing bisphenol A in a crystallization device and continuously forming a slurry containing adduct crystals comprising phenol and bisphenol A, (3) a solid-liquid separation step of separating the adduct crystals from the formed slurry, and (4) a step of producing bisphenol A by removing phenol from the separated adduct crystals, wherein the crystallization step is performed by using a multi-chamber-type crystallization device having its inside divided into 3 or more compartments by partitions with at least one of the compartments equipped with a cooler, in which the phenolic solution containing bisphenol A is fed into one compartment in the crystallization device, the produced slurry of adduct crystals is sequentially transported into each compartment, and then the temperature of the slurry in the following stage is controlled to be lower than that in the previous stage to gradually cool the slurry containing adduct crystals in at least one set of two serial compartments.

BEST MODE FOR CARRYING OUT THE INVENTION

Bisphenol A can be produced by the dehydration condensation reaction of acetone with an excess amount of phenol in the presence of acid catalysts. The molar ratio of phenol to acetone is usually in the range of 3 to 30, and preferably 5 to 20. The reaction temperature is usually in the range of 40 to 120° C., and preferably 50 to 100° C.

Any one of homogeneous acids and solid acids can be used as the acid catalyst, but are not limited thereto. In view of low corrosiveness of devices and easiness in separating the catalyst from the reaction mixture, the solid acid catalyst is preferable.

In a method in which a homogeneous acid is used as a catalyst, hydrochloric acid, sulfuric acid and the like are generally used. Sulfuric acid which can be easily separated is preferably used.

In a method in which a solid acid is used as a catalyst, a sulfonic acid-type cation-exchange resin is generally used. In order to improve the catalytic activity of a sulfonic acid-type cation-exchange resin, a sulfonic acid-type cation-exchange resin and a compound containing a thiol group may coexist in the reaction system. As a method of allowing a sulfonic acid-type cation-exchange resin and a compound containing a thiol group to coexist, there can be mentioned a method of ionically or covalently binding a part of the sulfonic acid groups of a sulfonic acid-type cation-exchange resin with a compound containing a thiol group [the way of fixing thiol], and a method of feeding a compound containing a thiol group, which does not form a chemical bond with a sulfonic acid-type cation-exchange resin, together with raw materials into a reactor packed with a sulfonic acid-type cation-exchange resin [the way of adding thiol]. Any one of said methods may be used, but the way of fixing thiol which does not need a step of recovering a compound containing a thiol group is preferable. A method of ionically binding a thiol compound with a sulfonic acid-type cation-exchange resin is more preferable. A method of ionically binding a thiol compound with 3 to 40% of a sulfonic acid group is still preferable, and a method of ionically binding a thiol compound with 5 to 30% of a sulfonic acid group is even still preferable.

The reaction mixture obtained as described above usually includes, in addition to bisphenol A, unreacted acetone, unreacted phenol, water produced during the reaction, and other side-products. The main component of the side-products is 2-(2-hydroxyphenyl)-2-(4-hydroxyphenyl)propane, and in addition, it includes trisphenol, a polyphenol compound, a chroman compound, colored impurities and the like. The reaction mixture is separated from catalysts. The separated mixture is then cooled in a crystallization step, if necessary, after removing unreacted acetone and water produced during the reaction and a part of phenol, to form a slurry containing adduct crystals.

In the process of producing bisphenol A according to the present invention, the solution of bisphenol A in phenol used as a raw material for producing adduct crystals is not particularly limited, provided that the solution is a mixture obtained by reacting acetone with an excess amount of phenol as described above. However, the concentration of bisphenol A is 10 to 50% by weight, and preferably 15 to 45% by weight. When the concentration of bisphenol A is less than 10% by weight, the recovery rate of adduct crystals becomes low. When the concentration of bisphenol A is more than 50% by weight, the viscosity of the slurry becomes high, so that the transportation of the slurry becomes difficult. Raw materials for crystallization may include, in addition to phenol and bisphenol A, 5% by weight or less, preferably 3% by weight or less and more preferably 1% by weight or less of water, 3% by weight or less of acetone, and 20% by weight or less, preferably 15% by weight or less and more preferably 10% by weight or less of the side-products, which are produced in the synthetic reaction of bisphenol A. The temperature of a solution of bisphenol A in phenol fed into a crystallization step is not particularly limited, provided that the temperature is higher than temperature Ts [° C.] which causes no precipitation of adduct crystals. However, in the case where the solution is fed at higher temperatures than be needed, the heat transfer areas of a cooler become large, as well as the energy required for cooling becomes large. Thus, the temperature is preferably in the range of Ts to (Ts+40)° C., and more preferably Ts to (Ts+20)° C.

In the crystallization step according to the present invention, a solution of bisphenol A in phenol is continuously fed and is then cooled at the temperatures of at least two steps to form a slurry of adduct crystals. The crystallization step may be performed using a crystallization device in which one vessel is divided into a plurality of the compartments by means of partitions, or a device in which a plurality of crystallization devices is linked to each other by piping. In addition, the crystallization step is performed so that the value of B/A may be 0.7 or less when a solid fraction (weight of adduct crystals/weight of the total slurry) of the slurry is A [% by weight] in the final crystallization stage prior to transporting the slurry from a crystallization step into a solid-liquid separation step and is B [% by weight] in a crystallization stage (a first stage) in which adduct crystals are first formed. When the value of B/A exceeds 0.7, the amounts of impurities in adduct crystals obtained from the final crystallization stage become large. Therefore, the hue of the crystals becomes bad. In the case where the amount of adduct crystals produced in the first stage is too small, the efficiency of the device is lowered. Thus, the value of B/A is preferably in the range of 0.03 to 0.05, and more preferably 0.05 to 0.4. Values A and B are affected by various factors such as a temperature of adduct crystals and concentrations of bisphenol A, water, and impurities in raw materials for crystallization. But, in many cases, these factors except the temperature in the first stage may be generally determined by other processing factors. Accordingly, in order to set the range of B/A value to the above ranges, the value of B is manipulated by appropriately controlling the temperature of adduct crystals in the first stage to be within the above range.

An object of the present invention is to provide also a method in which the crystallization step is performed by using a multi-chamber type crystallization device having its inside divided into 3 or more compartments by partitions with at least one of the compartments equipped with a cooler, in which the phenolic solution containing bisphenol A is fed into one compartment in the crystallization device, the produced slurry of adduct crystals is sequentially transported into each compartment, and then the temperature of the slurry in the following stage was controlled to be lower than that in the previous stage to gradually cool the slurry containing adduct crystals in at least one set of two continuous compartments.

In the multi-chamber type crystallization device, the partitions are provided with an inlet port. The slurry is transported into a compartment of the next stage through the inlet port. Accordingly, it is unnecessary to use a pump in the transportation of the slurry between crystallization tanks, so that adduct crystals are not crushed by a transport pump. Thus, the amount of fine crystals produced is small. Further, it is possible to produce adduct crystals having high purity and an excellent hue using a simple and inexpensive device, as compared with the known method using a series of multi-stage crystallization tanks.

The number of compartments of the multi-chamber type crystallization device is not particularly limited, provided that the number of compartments is 3 or more. The number of compartments is preferably 3 to 50, and more preferably 7 to 40. When the number of compartments is less than 3, the purity and hue of crystals are insufficient. In the case where the number of compartments is more than 50, further improvement of the purity and the hue is not be expected. The multi-chamber type crystallization device has at least one cooler. Each compartment is not necessarily equipped with a cooler. It is however preferable to provide a cooler to each compartment since the precise control of the device temperature is possible. A slurry of adduct crystals is gradually cooled to a desired temperature using the cooler. The cooled slurry is then discharged from the multi-chamber type crystallization device.

Each compartment may be equipped with a stirrer for the promotion of mixing the slurry of adduct crystals. As a cooler, a cooler which uses cooling plates capable of flowing a cooling medium is preferable. Partitions, which divide the inside of a crystallization device into a plurality of compartments, may also function as cooling plates. In case of using partitions as cooling plates, all partitions do not necessarily function as a cooler, and a crystallization device in which a part of partitions optionally have a cooling function, may be used. The inner wall of the crystallization device may function as a cooler by the circulation of a cooling medium in a jacket provided in crystallization device. The jacket may be use in combination with other coolers. In addition, it is possible to use a method comprising discharging a part of a slurry from at least one compartment in a crystallization device provided with a cooler in the outside thereof and cooling the discharged slurry in the cooler and then recycling the cooled slurry to the same compartment or the compartment of the next stage. However, since the adduct crystals are crushed by a pump, etc. in the case of carrying out the recycling step, a method using the above partitions as cooling plates or a method using a jacket as a cooler is preferable.

Since adduct crystals having high purity and an excellent hue can be obtained by using the multi-chamber type crystallization device of the present invention, as compared with the known method of crystallizing a solution of bisphenol A in phenol using a series of multi-stage crystallization tanks, it is possible to increase the temperature difference between the cooling surface of a cooler and the slurry of adduct crystals present in the same compartment as the cooling surface, compared with temperature difference in the known process. In addition, one of the features of the present invention is that it is possible to reduce heat transfer areas of a cooler. For example, PCT Japanese Translation Patent Publication NO. 2003-528840 discloses that the temperature difference is preferably in the range of 2 to 6 [K]. However, the temperature difference in crystallization devices according to the present invention is 15° C. or less, and preferably 10° C. or less. When the temperature difference between a cooling surface of a cooler and the slurry of adduct crystals present in the same compartment as the cooling surface is 15° C. or less, it is possible to produce adduct crystals having high purity, an excellent hue, and a small amount of fine crystals. In addition, it is difficult that adduct crystals adhere to the cooling surface. Here, in the case where the cooler is a cooler which allows a cooling medium to flow therein, the temperature of the cooling surface may be considered to be substantially the same as that of the cooling medium which is flowed in the cooler.

The method of feeding a cooling medium is not limited, provided that the temperature difference between the cooling surface of a cooler and the slurry of adduct crystals present in the same compartment as the cooling surface is within the above range. The cooling medium may be separately fed into a cooler of each compartment, or the cooling medium may be fed in single operation into one cooler and then the used cooling medium may be fed into another cooler. The preferable embodiment is a method in which at least a part of the cooling medium is used countercurrently with respect to the flow of the slurry of adduct crystals. As such method, there can be mentioned, for example, a method comprising:

when feeding the slurry of adduct crystals into the first compartment and sequentially transporting the produced slurry of adduct crystals into each compartment until the slurry reaches the final compartment while gradually cooling, feeding a cooling medium into the cooler provided in the final compartment and then discharging it therefrom, sequentially transporting the cooling medium into a cooler of each compartment in the opposite direction to the flow of the slurry of adduct crystals, using the transported cooling medium in the cooler of the first compartment where the slurry is fed, and finally discharging the used cooling medium. In case of performing this method, it is not necessary to use a device for separately controlling the temperature of the cooling medium, and it is economical. The cooling medium is not particularly limited, but is for example, water, an aqueous ethylene glycol solution, an aqueous propylene glycol solution, an aqueous phenolic solution or the like can be used.

In the method using a multi-chamber type crystallization device for producing bisphenol A of the present invention, in the case where it is necessary to stably perform crystallization operation for a longer term, the places where the cooling surface of a cooler comes into contact with a slurry of adduct crystals may be equipped with a device preventing adduct crystals from adhering to the surface. As a method using a device which prevent adduct crystals from adhering to the surface, there can be mentioned a method of forming the flow of slurry on the surface of cooling plates and a method of providing a device counter-transporting while coming into contact with the cooling surface of a cooler, as disclosed in U.S. Pat. No. 6,090,972 and U.S. Pat. No. 6,100,422, respectively. As the following method, for example, there can be mentioned a method wherein cooling plates also functioning as partitions which allows a cooling medium to be flowed in are arranged in parallel in a crystallization device and the surface of cooling plates is scraped by a wiper linked to a shaft, as disclosed in U.S. Pat. No. 6,355,218 and U.S. Pat. No. 4,486,395. In addition, a "Cooling Disc Crystallizer" available from GMF GOUDA can be suitably used. In the case of using the device counter-transporting while coming into contact with the cooling surface, the frequency of bringing the cooling surface into contact with a device preventing adduct crystals from adhering to the surface is set to 0.1 to 30 times per minute, and preferably 0.5 to 15 times per minute. When the frequency is less than 0.1 times per minute, the effect of a device preventing adduct crystals from adhering to the surface is insufficient, while when the frequency is more than 30 times per minute, the power required to scrape the adhered crystals off becomes large.

The multi-chamber type crystallization device can also be suitably used in the process of producing according to the present invention wherein a solution of bisphenol A in phenol is cooled at the temperatures of at least two steps to form a slurry containing adduct crystals, the at least two crystallization stages having different temperatures from each other are provided, and the value of B/A is 0.7 or less when the solid fraction of the slurry is A [% by weight] in the final crystallization stage prior to transporting the slurry into a solid-liquid separation step and is B [% by weight] in the crystallization stage in which crystals are first formed. In this case, the multi-chamber type crystallization device may be used in all of the first stage to the final stage, but it is not always necessary to do so. When a solid fraction of the slurry is C [% by weight] in each crystallization stage and compartment, from the first stage to the stage having the value of C/A of at least 0.3, preferably at least 0.5 and more preferably at least 0.7, such stages may be performed by the multi-chamber type crystallization device. By using the multi-chamber type crystallization device from the first stage to the stage having the value of C/A of at least 0.3, the precise control of a temperature according to a growth process of crystals growth becomes easier to obtain adduct crystals having excellent purity and an excellent hue. In addition, the formation of fine crystals is prevented. In this case, the value of B is the solid fraction of the compartment, in which crystals are first formed, in the multi-chamber type crystallization tank. The relation between B and C is B<C. The relation between B and C is not particularly limited except that mentioned above. However, when B/C is preferably 0.7 or less and more preferably 0.5 or less, adduct crystals having higher purity and better hue can be obtained.

The temperature difference between the slurries of adduct crystals present in two serial crystallization stages or compartments is preferably 10° C. or less, still preferably 8° C. or less, and even still preferably 0.5 to 5° C. When the temperature difference is within the above range, the purity and the hue can become better. In particular, in an initial crystallization stage or compartment having a value of C/A of less than 0.4, it is particularly preferable to maintain the temperature difference 10° C. or less.

On the other hand, as the temperature difference is smaller, the purity and the hue of crystals are improved, but the number of crystallization stages and compartments however becomes large, so that the process becomes complex. For more economical performances, while the temperature difference in an initial crystallization stage or compartment is maintained within the above range, two serial crystallization devices or compartments in which the temperature difference $\Delta T$ between the slurries of a previous crystallization stage or compartment and a following crystallization stage or compartment exceeds 10° C. may be present in the crystallization stage or compartment wherein the value of C/A is 0.4 or more, preferably 0.5 or more, and more preferably 0.7 or more. By this, it is possible to simplify the crystallization step without afflicting severe damage to the purity and the hue of adduct crystals.

In addition, in at least one set of two serial crystallization stages or compartments, it is necessary that the temperature of the slurry in the following stage is controlled to be lower than that in the previous stage. However, in a part of the crystallization stages or compartments, the temperatures in the previous stage and the following stage may be identical or the temperature in the following stage may be higher by 5° C. or less than that in the previous stage.

In any method used in the present invention, the total residence time of the slurry of adduct crystals is 0.5 to 8 hours, preferably 1 to 4 hours, and more preferably 1 to 3 hours. In the case where the residence time is less than 0.5 hour, the purity and the hue of crystals are insufficient, while in the case of more than 8 hours, the purity and the hue are also not substantially improved. The temperature of the slurry of adduct crystals in the final compartment is not particularly limited, but is usually 40 to 70° C. The concentration of the slurry of adduct crystals is not particularly limited, provided that the concentration is one capable of transporting the slurry of adduct crystals. The concentration of the slurry in the final compartment is usually 10 to 60% by weight and preferably 10 to 50% by weight.

The slurry of adduct crystals discharged from the final crystallization stage is fed into a solid-liquid separation step to be separated into adduct crystals and a mother liquor. Moreover, the adduct crystals are washed with phenol, etc. in order to remove a mother-liquor adhered thereto. The adduct crystals obtained by the process of producing according to the present invention have high purity and an excellent hue in themselves, have a small amount of fine crystals and are obtained as large crystals, so that solid-liquid separation and washing are easy. Bisphenol A is recovered by removing phenol from the adduct crystals obtained from the solid-liquid separation and washing processes. Since the adduct crystals have high purity and an excellent hue, bisphenol A obtained by the process of the present invention has high purity and a good hue and is suitable for raw materials of polymers such as aromatic polycarbonate.

EXAMPLES

The present invention will be described below with reference to the following examples. In addition, the hue of adduct crystals was determined by thoroughly dissolving 30 g of adduct crystals in 30 ml of ethanol and measuring the absorbance at 420 nm by a spectrophotometer and then converting the measured absorbance into the value of APHA by a calibration curve constructed from the absorbance of an APHA standard solution. The rate of adduct crystals having a particle size of 100 µm or less was calculated with the amount of crystals passing through a sieve having an opening size of 100 µm. The hue of bisphenol A was determined by comparing it with that of the APHA standard solution by visual inspection.

Example 1

A crystallization device, in which two crystallization tanks equipped with a stirrer having draft tubes therein were connected in series, was used. Phenolic solutions containing 35% by weight of bisphenol A and 5% by weight of the side-products of bisphenol A were continuously fed into the crystallization device at 90° C. so that the residence time in each crystallization tank might be one hour. The fed solutions were cooled so that the temperatures of slurries of adduct crystals in the crystallization tank in the first stage and the temperatures of the crystallization tank in the second stage might be 72° C. and 50° C., respectively. When the device was stabilized, the slurries of adduct crystals in each stage were collected to measure the solid fractions. As a result, the solid fraction B in the first stage and the solid fraction B in the second stage were 27% by weight and 42% by weight, respectively, and the value of B/A was 0.64. In addition, the rate of fine crystals having a particle size of 100 µm or less in the crystallization tank in the second stage was 18% by weight. The slurry of adduct crystals discharged from the crystallization tank in the second stage was centrifuged to recover crystals and the crystals were then washed with phenol. These adduct crystals had an APHA color of 9. Bisphenol A was obtained by removing phenol from the adduct crystals. The obtained bisphenol A had a good hue with an APHA color of 15.

Example 2

The same procedure was repeated in the same manner as in Example 1 except that the temperature of the crystallization tank in the first stage was 76° C. At this time, the value of B was 21% by weight and the value of B/A was 0.50. The rate of fine crystals having a particle size of 100 µm or less in adduct crystals obtained from the crystallization tank in the second stage was 15% by weight. The obtained crystals had an APHA color of 7.

Comparative Example 1

The same procedure was repeated in the same manner as in Example 1 except that the temperature of the crystallization tank in the first stage was 63° C. At this time, the value of B was 36% by weight and the value of B/A was 0.86. The rate of fine crystals having a particle size of 100 µm or less in adduct crystals obtained from the crystallization tank in the second stage was 27% by weight. The obtained crystals had an APHA color of 17. The bisphenol A obtained by removing phenol from the adduct crystals had a high value of hue with an APHA color of 35.

Example 3

A crystallization device, in which 5 partitions having an inlet port for transporting the slurry were introduced in parallel with each other at same intervals into a horizontal cylindrical-type vessel to divide the vessel into 6 cylindrical compartments having a same volume, each compartment being equipped with a jacket capable of flowing water as a cooler, was used. In order to stir the inside of each compartment, a shaft was provided on the central axis of the cylindrical vessel and the shaft was then equipped with an agitator blade to stir at 10 rpm. Water for cooling the slurry was fed into each jacket. Then, phenolic solutions containing 35% by weight of bisphenol A and 5% by weight of the side-products of bisphenol A were continuously fed at 85° C. into a compartment in the last end of this crystallization device. The produced adduct crystals were sequentially transported into the following compartments and then were discharged from the compartment in the last end (the final compartment) of the other side so that the residence time in a crystallization device might be 2 hours. The temperatures of adduct crystals in each compartment were 81, 77, 72, 66, 58 and 50° C. from the upstream side, respectively. The temperatures of the cooling water in the inlet of each compartment were 76, 72, 67, 61, 53 and 45° C. from the upstream side, respectively. The temperature difference between the cooling surface and the slurry was 5° C. When the device was stabilized, the slurry of adduct crystals was collected to measure the solid fraction. As a result, the solid fraction B in the first compartment was 11% by weight, the solid fraction A in the 6-th compartment which was the final compartment was 42% by weight and the value of B/A was 0.26. The rate of fine crystals having a particle size of 100 µm or less in the 6-th compartment was 5% by weight. Moreover, the crystals were recovered by centrifuging the slurry of adduct crystals discharged from the final compartment, and then were washed with phenol. These crystals had an APHA color of 2. In this state, the operation was continued for 100 hours, there was however no change in the hue of crystals and the rate of fine crystals having a particle size of 100 μm or less. The increase in the slurry temperature in the final compartment which was observed in the case where crystals were adhered to a cooling surface was also not observed.

Example 4

The same procedure was repeated in the same manner as in Example 1 except that, while the temperatures of adduct crystals in each compartment were maintained as the same temperatures described in Example 3 which were 81, 77, 72, 66, 58 and 50° C., the temperatures of cooling water in the inlet of each compartment were set to 69, 65, 60, 54, 46 and 38° C. from upstream side of slurry, respectively and the temperature difference between cooling surfaces and slurries became 12° C. by means of controlling the area of cooling surface in each compartment. When the crystallization device was stabilized, the obtained crystals had an APHA color of 5 and the rate of fine crystals having a particle size of 100 μm or less was 11 percent. In this state, the operation was continued for 100 hours, and as a result, the temperature of slurry in the final compartment was 51° C.

Example 5

The same solution of bisphenol A in phenol as in Example 1 was fed at 90° C. into the multi-chamber type crystallization device used in Example 3 so that the residence time might be one hour. The temperatures of the slurry of adduct crystals in each compartment were set to 83, 82, 80, 78, 75 and 72° C. from the upstream side, respectively. At this time, each temperature difference between cooling surfaces and the slurries became 5° C. In addition, the slurry discharged from the final compartment was fed into one crystallization tank used in Example 1 to perform crystallization at a slurry temperature of 50° C. during a residence time of 1 hour. At this time, the solid fraction B in the first compartment of the multi-chamber type crystallization device was 4% by weight. The solid fraction C in the final compartment was 27% by weight. The solid fraction A in the stirred crystallization tank equipped with draft tubes, which was in the final crystallization stage, was 42% by weight. The values of B/A and C/A were 0.10 and 0.64, respectively. The rate of fine crystals having a particle size of 100 μm or less in the final crystallization stage was 7% by weight. The crystals were recovered by centrifuging the slurry of adduct crystals discharged from the final crystallization stage and then washed with phenol. These crystals had an APHA color of 3. The multi-chamber type crystallization device was used until the value of C/A reached 0.3 or more. As a result, it was found that the hue of adduct crystals was improved as compared with that in Example 1 and the rate of fine crystals was decreased. In addition, as compared with Example 3, although the temperature difference ΔT between the slurries of the previous stage and the following stage was more than 10° C. after exceeding a value of C/A of 0.4, it was found that there was no substantial effect on the hue of adduct crystals and the rate of fine crystals.

Example 6

A crystallization device in which 7 partitions having an inlet port for transportation of a slurry were introduced in parallel with each other at same intervals into a horizontal cylindrical-type vessel to divide the vessel into 8 cylindrical compartments having the same volume, each compartment being equipped with a jacket capable of flowing water as a cooler, was used. In order to stir the inside of each compartment, a shaft was provided on the central axis of the cylindrical vessel and the shaft was then equipped with an agitator blade to stir at 10 rpm. Crystallization was then performed in the same manner as in Example 3 except that the temperatures of adduct crystals in each compartment were set to 82, 80, 76, 72, 67, 62, 56 and 50° C. from the upstream side, respectively, the temperatures of the cooling water in the inlet of each compartment were set to 77, 75, 71, 67, 62, 57, 51 and 45° C. from the upstream side, respectively, and the temperature difference between cooling surfaces and slurries became 5° C. When the device was stabilized, the slurry of adduct crystals was collected to measure the solid fraction. As a result, the solid fraction B in the first compartment was 9% by weight, the solid fraction A in the 8-th compartment which was the final compartment was 42% by weight and the value of B/A was 0.21. The rate of fine crystals having a particle size of 100 μm or less in the 8-th compartment was 3% by weight. The crystals were recovered by centrifuging the slurry of adduct crystals discharged from the final compartment and then washed with phenol. The obtained crystals had an APHA color of less than 2. In this state, the operation was continued for 100 hours, there was however no change in the hue of crystals and the rate of fine crystals having a particle size of 100 μm or less, and further the increase in the slurry temperature was also not observed.

Example 7

By means of controlling the flow rate of the cooling water and the area of cooling surface in each compartment, the temperatures of adduct crystals in each compartment were set to 82, 79, 66, 61, 58, 55, 52 and 50° C. from upstream side of the slurry, respectively, and the temperature difference between the second compartment and the third compartment was 12° C. At this time, the temperatures of the cooling water in the inlet of each compartment were set to 77, 70, 56, 56, 55, 52, 49 and 47° C. from the upstream side of the slurry of adduct crystals, respectively, and the temperature difference between cooling surfaces and slurries was at most 10° C. Crystallization was then performed in the same manner as in Example 3 except the above-mentioned description. When the device was stabilized, the slurry of adduct crystals was collected to measure the solid fraction. As a result, the solid fraction C in the second compartment was 16% by weight, the solid fraction A in the 8-th compartment which was the final compartment was 42% by weight and the value of C/A was 0.38. The rate of fine crystals having a particle size of 100 μm or less in the 8-th compartment was 13% by weight. The crystals obtained by centrifuging the slurry of adduct crystals discharged from the 8-th compartment had an APHA color of 6.

Reference Example

By using only one of the crystallization devices used in Example 1, the same solution of bisphenol A in phenol as in Example 1 was continuously fed so that the residence time might be 2 hours. The crystallization tank was then cooled until the inside temperature reached 50° C. When the device was stabilized, the slurry of adduct crystals discharged from the lower portion of the crystallization tank was centrifuged to recover crystals. These crystals had an APHA color of 23. The rate of fine crystals having a particle size of 100 μm or less was 36% by weight.

INDUSTRIAL APPLICABILITY

According to the present invention, it is possible to provide a process of producing bisphenol A which excels in economical efficiency and has high purity and an excellent hue.

What is claimed is:

1. A process of producing bisphenol A comprising:
   (A) a step of producing a phenolic solution containing bisphenol A by reacting phenol with acetone,
   (B) a crystallization step of cooling the obtained phenolic solution containing bisphenol A in a crystallization device and continuously forming a slurry containing adduct crystals comprising phenol and bisphenol A,
   (C) a solid-liquid separation step of separating the adduct crystals from the slurry, and
   (D) a step of producing bisphenol A by removing phenol from the adduct crystals,
   wherein, in the crystallization step,
   (a) the fed solution of bisphenol A in phenol is cooled at temperatures of at least two steps to form a slurry containing adduct crystals,
   (b) at least two crystallization stages having different cooling temperatures are provided, and
   (c) when the solid fraction of the slurry is A [% by weight] in the final crystallization stage prior to transporting the slurry into the solid-liquid separation step and is B [% by weight] in the crystallization stage in which crystals are first formed, the value of B/A is kept at 0.7 or less.

2. A process of producing bisphenol A comprising:
   (A) a step of producing a phenolic solution containing bisphenol A by reacting phenol with acetone,
   (B) a crystallization step of cooling the obtained phenolic solution containing bisphenol A in a crystallization device and continuously forming a slurry containing adduct crystals comprising phenol and bisphenol A,
   (C) a solid-liquid separation step of separating the adduct crystals from the formed slurry,
   (D) a step of producing bisphenol A by removing phenol from the separated adduct crystals,
   wherein the crystallization step is performed by using a multi-chamber-type crystallization device having its inside divided into 3 or more compartments by partitions with at least one of the compartments equipped with a cooler, in which the phenolic solution containing bisphenol A is fed into one compartment in the crystallization device, the produced slurry of adduct crystals is sequentially transported into each compartment, and then the temperature of the slurry in the following stage is controlled to be lower than that in the previous stage to gradually cool the slurry containing adduct crystals in at least one set of two serial compartments, and
   wherein, in the crystallization step,
   (a) the fed solution of bisphenol A in phenol is cooled at temperatures of at least two steps to form a slurry containing adduct crystals,
   (b) at least two crystallization stages having different cooling temperatures are provided, and
   (c) when the solid fraction of the slurry is A (% by weight) in the final crystallization stage prior to transporting the slurry into the solid-liquid separation step and is B (% by weight) in the crystallization stage in which crystals are first formed, the value of B/A is kept at 0.7 or less.

3. The process according to claim 1, comprising feeding the phenolic solution containing bisphenol A into one compartment of the crystallization device to produce a slurry of adduct crystals, sequentially transporting the produced slurry of adduct crystals to each compartment, and gradually cooling the slurry of adduct crystals, by using a multi-chamber type crystallization device having its inside divided into 3 or more compartments by partitions with at least one of the compartments equipped with a cooler is used, until the value of C/A is at least 0.3 when the solid fraction in the slurry is A [% by weight]in the final crystallization stage prior to transporting the slurry into the solid-liquid separation step and the solid fraction in the slurry is C [% by weight ]in each crystallization stage.

4. The process according to any one of claims 1 to 3, wherein the temperature difference between the slurries of adduct crystals present in two serial crystallization stages or compartments is 10° C. or less.

5. The process according to claim 4, wherein when the solid fraction in the slurry is A [% by weight ]in the final crystallization stage prior to transporting the slurry from the crystallization step into the solid-liquid separation step and the solid fraction in the slurry is C [% by weight ]in each crystallization stage or compartment, the crystallization stages or compartments having the value of C/A of 0.4 or more have at least one set of two serial crystallization stages or compartments having a temperature difference DT between the slurries of the previous stage or compartment and the following stage or compartment of more than 10° C.

6. The process according to any one of claims 1 to 3, wherein in a multi-chamber crystallization device, the temperature difference between the cooling surface of a cooler and the slurry of adduct crystals present in the same compartment as the cooling surface is 15° C. or less.

7. The process according to any one of claims 1 to 3, wherein a device is provided, which prevents adduct crystals of phenol-bisphenol A from adhering to the cooling surface.

8. The process according to claim 1, wherein, in the crystallization step, the total residence time of the slurry of adduct crystals is 1 to 3 hours.

9. The process according to claim 2, wherein, in the crystallization step, the total residence time of the slurry of adduct crystals is 1 to 3 hours.

* * * * *

UNITED STATES PATENT AND TRADEMARK OFFICE
CERTIFICATE OF CORRECTION

| | | |
|---|---|---|
| PATENT NO. | : 7,598,424 B2 | Page 1 of 1 |
| APPLICATION NO. | : 10/542797 | |
| DATED | : October 6, 2009 | |
| INVENTOR(S) | : Hideaki Nakamura | |

It is certified that error appears in the above-identified patent and that said Letters Patent is hereby corrected as shown below:

<u>In Claim 5, Column 14, Line 38</u>:

Change "DT" to --$\Delta T$--.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO.        : 7,598,424 B2                                   Page 1 of 1
APPLICATION NO.   : 10/542797
DATED             : October 6, 2009
INVENTOR(S)       : Hideaki Nakamura It is certified that error appears in the above-identified patent and that said Letters Patent is hereby corrected as shown below:

IN THE CLAIMS:

In claim 7, at column 14, line 48, after "cooling surface", insert --of the cooler--.

Signed and Sealed this
Thirty-first Day of March, 2015

Michelle K. Lee
*Director of the United States Patent and Trademark Office*